US007863243B2

(12) United States Patent
Matsuzawa et al.

(10) Patent No.: US 7,863,243 B2

(45) Date of Patent: Jan. 4, 2011

(54) ANTI-TUMOR AGENT

(75) Inventors: Yuji Matsuzawa, Takarazuka (JP); Tohru Funahashi, Suita (JP); Shinji Tamura, Minoh (JP)

(73) Assignee: Sankyo Company, Limited, Tokyo (JP)

( * ) Notice: Subject to any disclaimer, the term of this patent is extended or adjusted under 35 U.S.C. 154(b) by 201 days.

(21) Appl. No.: 11/414,100

(22) Filed: Apr. 28, 2006

(65) Prior Publication Data

US 2006/0247169 A1 Nov. 2, 2006

(30) Foreign Application Priority Data

Nov. 4, 2003 (JP) ............................ 2003-375021

(51) Int. Cl.
*A61K 38/00* (2006.01)

(52) U.S. Cl. ........................................ 514/12; 530/350

(58) Field of Classification Search ....................... None
See application file for complete search history.

(56) References Cited

FOREIGN PATENT DOCUMENTS

| | | | |
|---|---|---|---|
| EP | 1 365 022 | A1 | 11/2003 |
| EP | 1 393 739 | A1 | 3/2004 |
| EP | 1 589 106 | A1 | 10/2005 |
| JP | 2000-256208 | | 9/2000 |
| JP | 2002-515452 | | 5/2002 |
| JP | 2002-517259 | A | 6/2002 |
| JP | 2002-363094 | A | 12/2002 |
| JP | 2003-527067 | A | 9/2003 |
| JP | 2004-331570 | | 11/2004 |
| JP | 2004-345968 | | 12/2004 |
| WO | WO 99/59618 | A1 | 11/1999 |
| WO | WO 99/59619 | A1 | 11/1999 |
| WO | WO 99/64629 | A1 | 12/1999 |
| WO | WO 02/061076 | A1 | 8/2002 |
| WO | WO 02/072149 | A1 | 9/2002 |
| WO | 03/062275 | * | 7/2003 |
| WO | 2004/063711 | * | 7/2004 |
| WO | WO 2004/061108 | A1 | 7/2004 |
| WO | WO 2005/031345 | | 4/2005 |

OTHER PUBLICATIONS

Skolnick et al. (Trends in Biotech., 18(1):34-39, 2000).*
Matsuzawa, Accession No. 2005:43451, 2005 (abstract only).*
Tamura et al Adiposcience (2005) 2(2): 122-127.*
Translation of Tamura et al Adiposcience (2005) 2(2): 122-127.*
Essell (J. NIH Res. 1995 7:46).*
Spitler (Cancer Biotherapy, 1995, 10:1-3).*
Boon (Adv. Can. Res. 1992 58:177-210.*
Waki et al., "Impaired Multimerization of Human Adiponectin Mutants Associated with Diabetes," Journal of Biological Chemistry, vol. 278, No. 41, pp. 40352-40363, 2003.
Pajvani et al., "Structure-Function Studies of the Adipocyte-secreted Hormone Acrp30/Adiponectin," Journal of Biological Chemistry, vol. 278, No. 11, pp. 9073-9085, 2003.
Scherer et al., "A Novel Serum Protein Similar to Clq, Produced Exclusively in Adipocytes," Journal of Biological Chemistry, vol. 270, No. 45, pp. 26746-26749, 1995.
Kamada et al., "Enhanced Carbon Tetrachloride-Induced Liver Fibrosis in Mice Lacking Adiponectin," Gastroenterology vol. 125, pp. 1796-1807, 2003.
Maeda et al., "Diet-induced Insulin Resistance in Mice Lacking Adiponectin/ACRP30," Nature Medicine, vol. 8, No. 7, 2002.
Nakae et al., "High Incidence of Hepatocellular Carcinomas Induced by a Choline Deficient L-Amino Acid Defined Diet in Rats," Cancer Research 52, pp. 5042-4045, 1992.
Xu et al. "The Fat-derived Hormone Adiponectin Alleviates Alcoholic and Nonalcoholic Fatty Liver Diseases in Mice," Journal of Clinical Investigation, vol. 112, No. 1, 2003.
Kamata, "P-129 Effects of Adiponectin in the Liver," Kanzo (肝臓: Liver), vol. 44, No. Supplement 2, p.A420, 2003.
WIPO, PCT Notification Concerning Transmittal of International Preliminary Report on Patentability dated May 18, 2006 and accompanying PCT International Preliminary Report on Patentability.
Kazuhisa Maeda et al. "cDNA Cloning And Expression Of A Novel Adipose Specific Collegen-like Factor, apMI (Adipose Most Abundant Gene Transcript 1)" *Biochemical and Biophysical Research Communications*, No. 0587, 221, pp. 286-289, (1990).
Yukio Arita et al. "Paradoxical Decrease Of An Adipose-Specific Protein, Adiponectin, In Obesity" *Biochemical and Biophysical Research Communications*, No. 257, pp. 79-83.
Yuji Matsuzawa "Adiponectin: Identification, Physiology And Clinical Relevance In Metabolic And Vascular Disease" *Atherosclerosis Supplements*, No. 6, pp. 7-14 (2005).
International Search Report for international application No. PCT/JP2004/015900, mailed on Dec. 14, 2004.
Kawata, Y. et al., "Controlling Effect of Adiponectin for a Liver Fat Deposition and a Liver Cancer Incidence", *Acta Hepatolobica Japonica*, 45(1):A41, WS-11, Apr. 2004.
Shimamora, I. et al., *The Journal of the Japanese Society of Internal Medicine*, 92(4), Apr. 2003, pp. 609-615.
Yoshiro Kamata, et al, "Effects of Adiponectin in the Liver" *Liver*, Sep. 30, 2003, vol. 44, Supplement 2, A420, P-129 (with English Translation).
Yoshiro Kamata, et al, "Suppression Effect of the Adipocyte Specific Protein Adiponectin (AN) on Liver Fibrosis" *Liver*, Sep. 30, 2002, vol. 43, Supplement 2, A268, S5-3 (with English Translation).
Norio Hayashi, Hepatology, Nihon-Yakuji-Shinpou, Feb. 8, 2003, vol. 4111, p. 14-20 (with English Translation).
Yasuo Miyoshi, et al, Serum Adiponectin Levels and Breast Cancer Risk, *Japanese Cancer Association Assembly Abstract*, Aug. 25, 2003, p. 88 assembly 1051-PA (with English Translation).
Kenta Motomura, "Relation of Diabetes and Obesity to Non-B, Non-C Hepatocellular Carcinoma", *The 7th Assembly of Japan Society of Hepatology Abstract*, Sep. 30, 2003, A389, P-7 (with English Translation).

* cited by examiner

*Primary Examiner*—Sheela J Huff
(74) *Attorney, Agent, or Firm*—Brandon T. Schurter; Locke Lord Bissell & Liddell, LLP

(57) ABSTRACT

The present invention provides a new anti-tumor agent containing adiponectin as an active ingredient, particularly, an anti-tumor agent capable of inhibiting carcinogenesis in the liver, use of adiponectin as an anti-tumor agent, and a prophylactic or therapeutic method against a tumor using adiponectin. The administration form may be either oral administration, e.g., by tablets or parenteral administration, e.g., by injection; in the case of intravenous injection for inhibiting carcinogenesis in the liver, the dosage is 1 to 100 mg/kg/day per adult patient.

2 Claims, 6 Drawing Sheets

ANTI-TUMOR AGENT

This application claims the benefit under 35 U.S.C. §120 and under 35 U.S.C. §365(c) of PCT/JP2004/015900, which was filed Oct. 27, 2004 designating the U.S., and claims the benefit under 35 U.S.C. §119(a)-(d) of Japanese Patent Application 2003-375021, filed Nov. 4, 2003. The contents of the prior applications are hereby incorporated by reference in their entirety.

TECHNICAL FIELD

The present invention relates to anti-tumor agents, particularly anti-liver tumor agents.

BACKGROUND ART

Adiponectin is a protein specific for animal adipose tissue first separated from human adipose tissue by Maeda et al. in 1996 (Maeda et al., Biochem. Biophys. Res. Commun., 221: 286, 1996). Adiponectin is present in abundance in blood as well as in adipose tissue, being found at a concentration as high as 5 to 10 μg/ml in normal human blood (Arita et al., Biochem. Biophys. Res. Commun., 257:79-83, 1999).

It is known that patients with obesity have a high prevalence of cancer and a reduced concentration of blood adiponectin (Arita et al., supra). Blood adiponectin has been previously shown to have the effects of inhibiting proliferation of monocytes- and B cells (Japanese Patent Laid-Open No. 2000-256208) and suppressing activation of hepatic stellate cells and production of extracellular matrixes (Japanese Patent Laid-Open No. 2002-363094). However, the relationship between blood adiponectin concentration and illness in obese patients has not sufficiently been demonstrated.

Thus, as a result of further advancing an investigation and study relating to the relationship between blood adiponectin concentration and illness, the present invention was completed by discovering that reduced blood adiponectin concentration promotes carcinogenesis.

An object of the present invention is to provide a new anti-tumor agent, in particular, an anti-tumor agent capable of inhibiting carcinogenesis in the liver, use of adiponectin as an anti-tumor agent, and a prophylactic or therapeutic method against a tumor using adiponectin.

DISCLOSURE OF THE INVENTION

Thus, the present invention relates to:

(1) an anti-tumor agent containing adiponectin as an active ingredient;

(2) manufacturing an anti-tumor agent containing adiponectin as an active ingredient; and (3) a method for preventing or treating a tumor by administering adiponectin.

A preferred target tumor is a liver tumor; adiponectin is preferably administered in the form of an injection; and the dosage is 1 to 100 mg/kg/day per adult patient. Other dosages for other ages may be used based on the above dosage schedule. For example, adiponectin may be administered in a dosage of from about 0.1 to about 100 mg/kg/day per individual. Alternatively, adiponectin may be administered in a dosage from about 1 to about 1000 mg/kg/day per individual.

According to the invention, a new anti-tumor agent is provided which can be applied clinically for prophylactic and therapeutic purposes against a tumor, as well as being expected to inhibit carcinogenesis in various organs including the liver.

DETAILED DESCRIPTION

Figure 1:
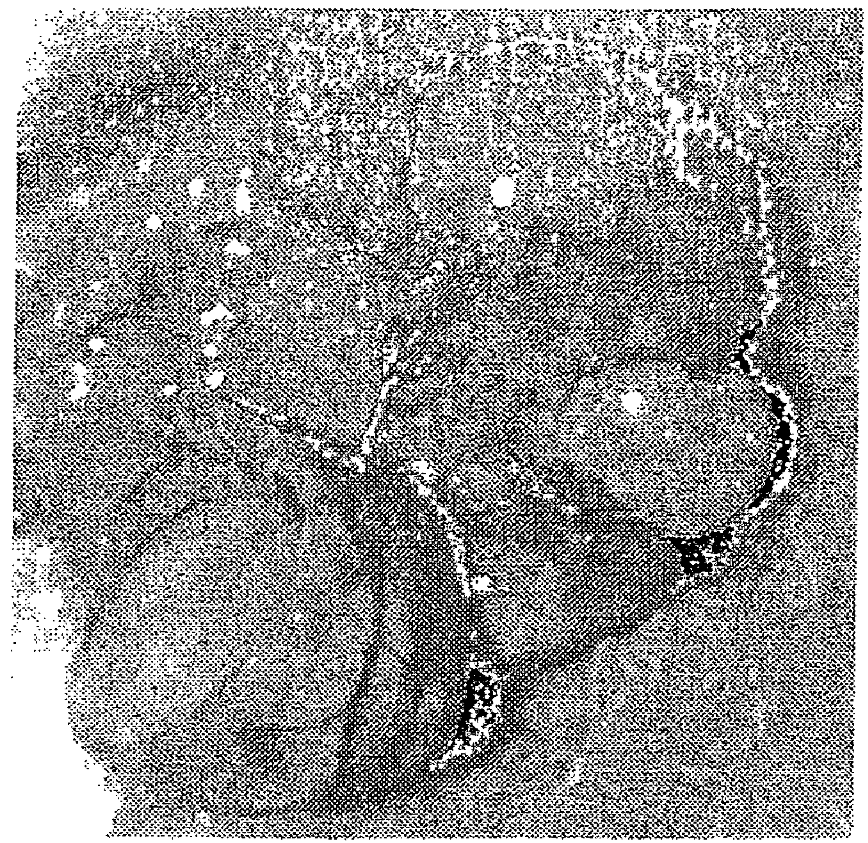
FIG. 1 is one example of each photograph showing an overview image of the liver after 6 months of administration of a CDAA diet. Development of cirrhosis and cancer of the liver was observed in KO mice, while only fatty liver developed in all WT mice (control mice)
Figure 1:
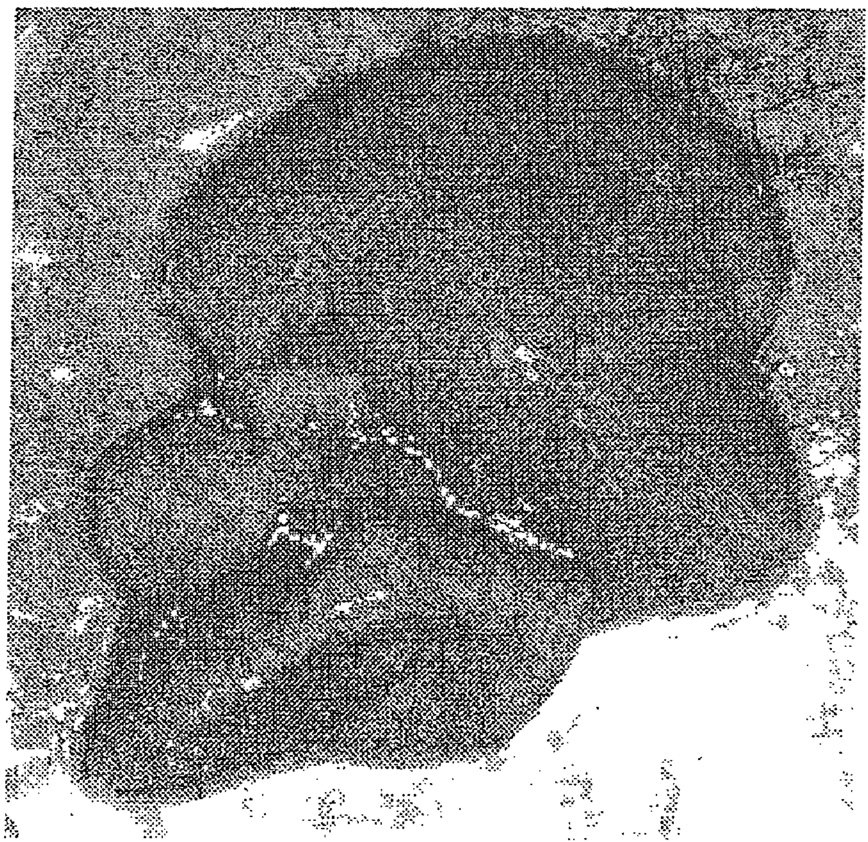
Figure 2:
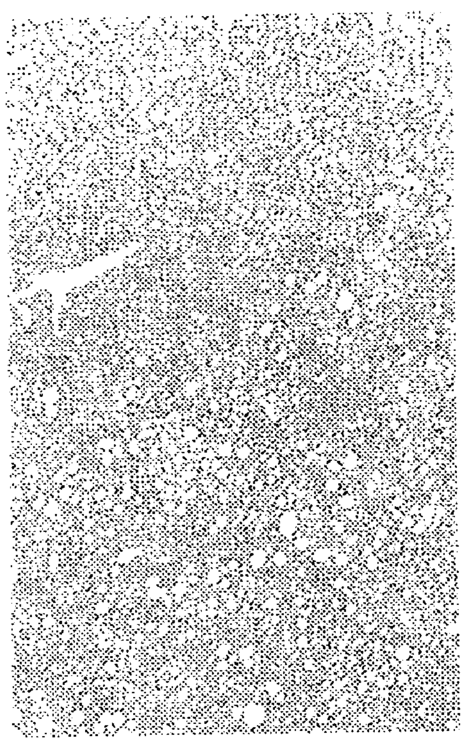
FIG. 2 is a set of liver histologies by HE staining after 6 months of administration of the CDAA diet. Infiltration of inflammatory cells, in addition to fatty liver, was found in KO mice, while only an image of pronounced fatty liver was observed in WT mice.
Figure 2:
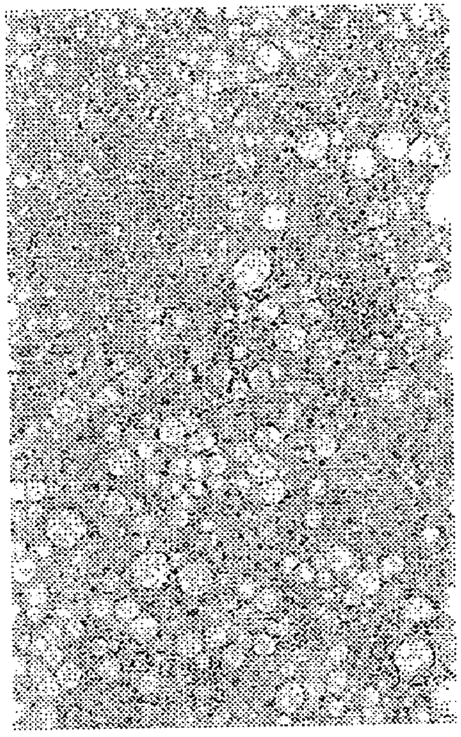
Figure 2:
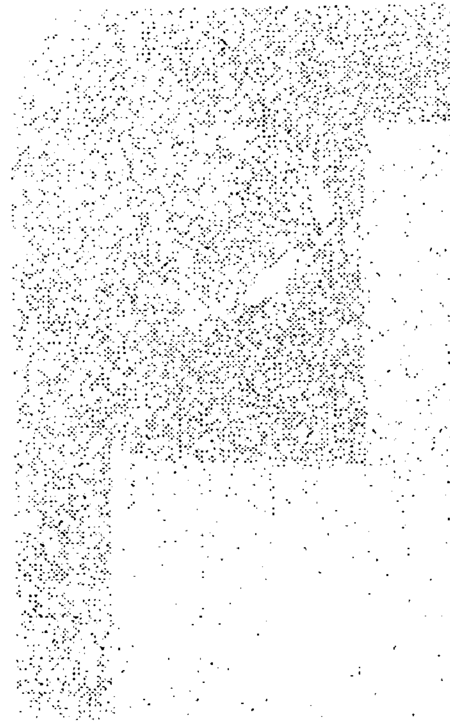
Figure 2:
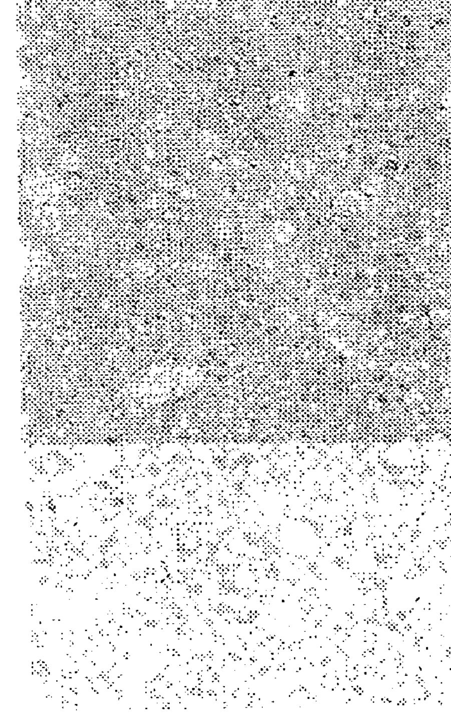
Figure 3:
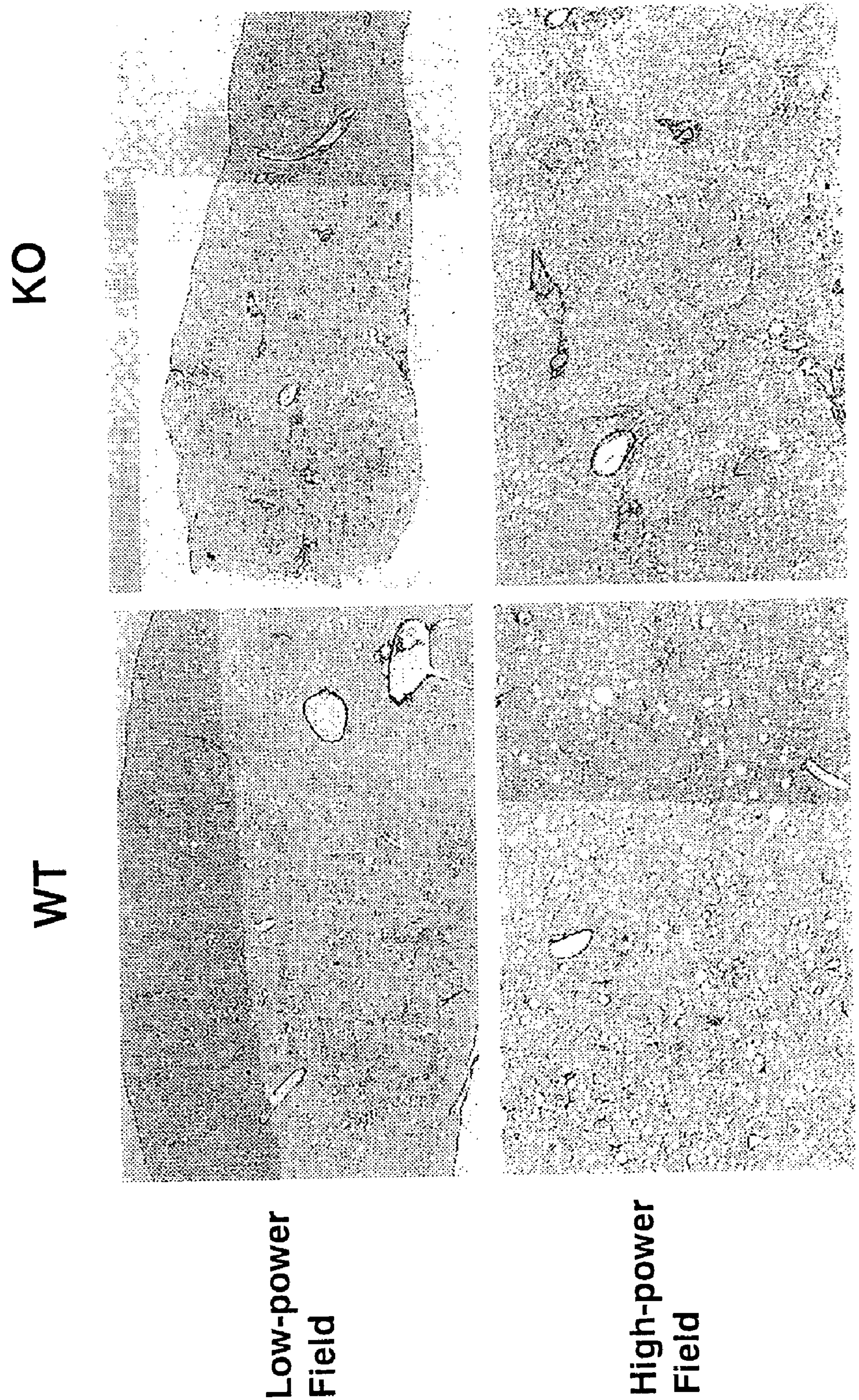
FIG. 3 is a set of liver histologies by Sirius Red staining after 6 months of administration of the CDAA diet. A high degree of fibrillation accompanied by bridge formation in the portal area was noted in KO mice, while only a minimal fibrillation was observed in WT mice.
Figure 4:
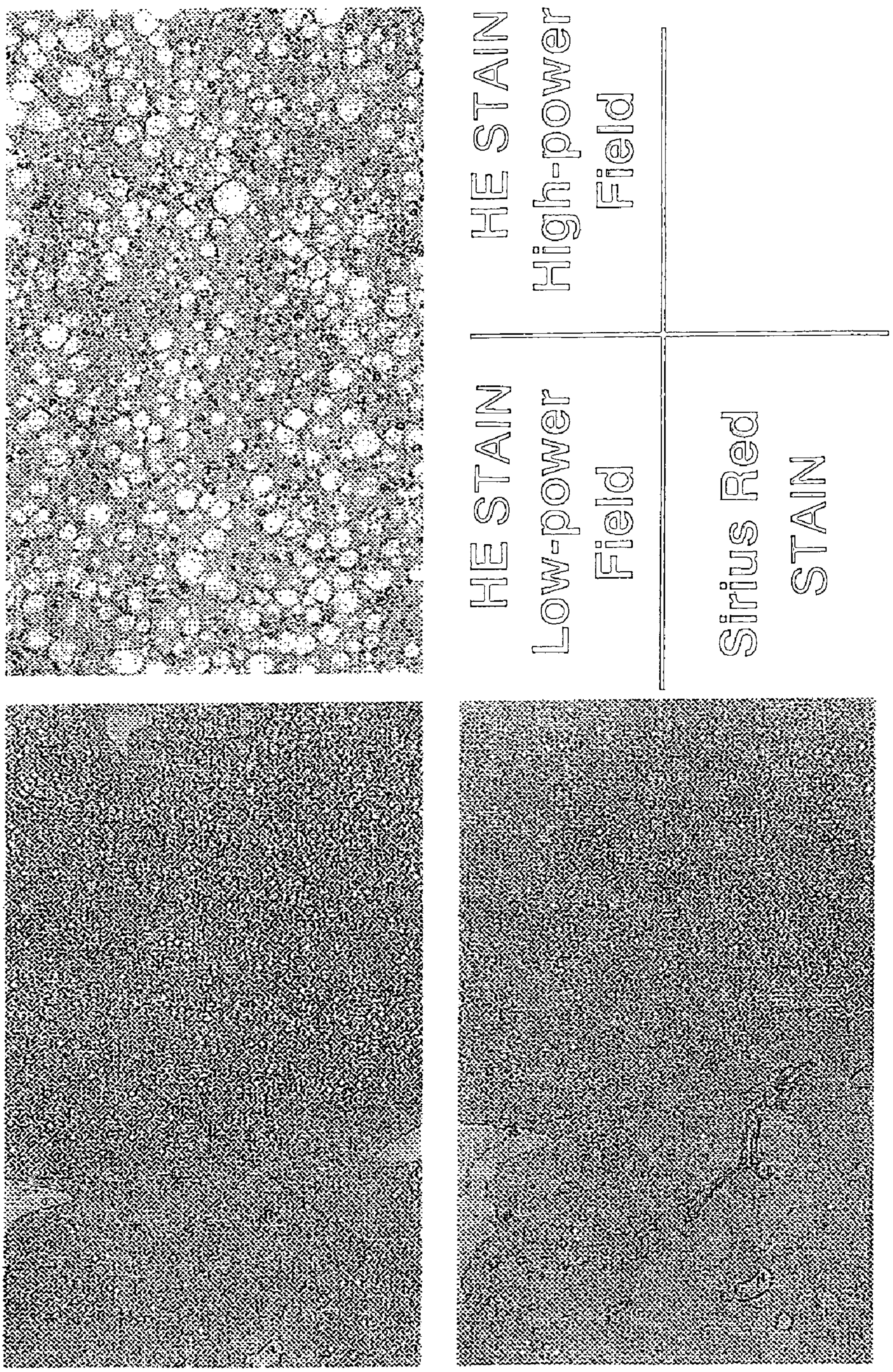
FIG. 4 is a set of histologies of a KO mouse liver tumor by HE and Sirius Red staining after 6 months of administration of the CDAA diet. This tumor showed an image of a well-differentiated fatty liver cell carcinoma accompanied by marked fatty degeneration.
Figure 5:
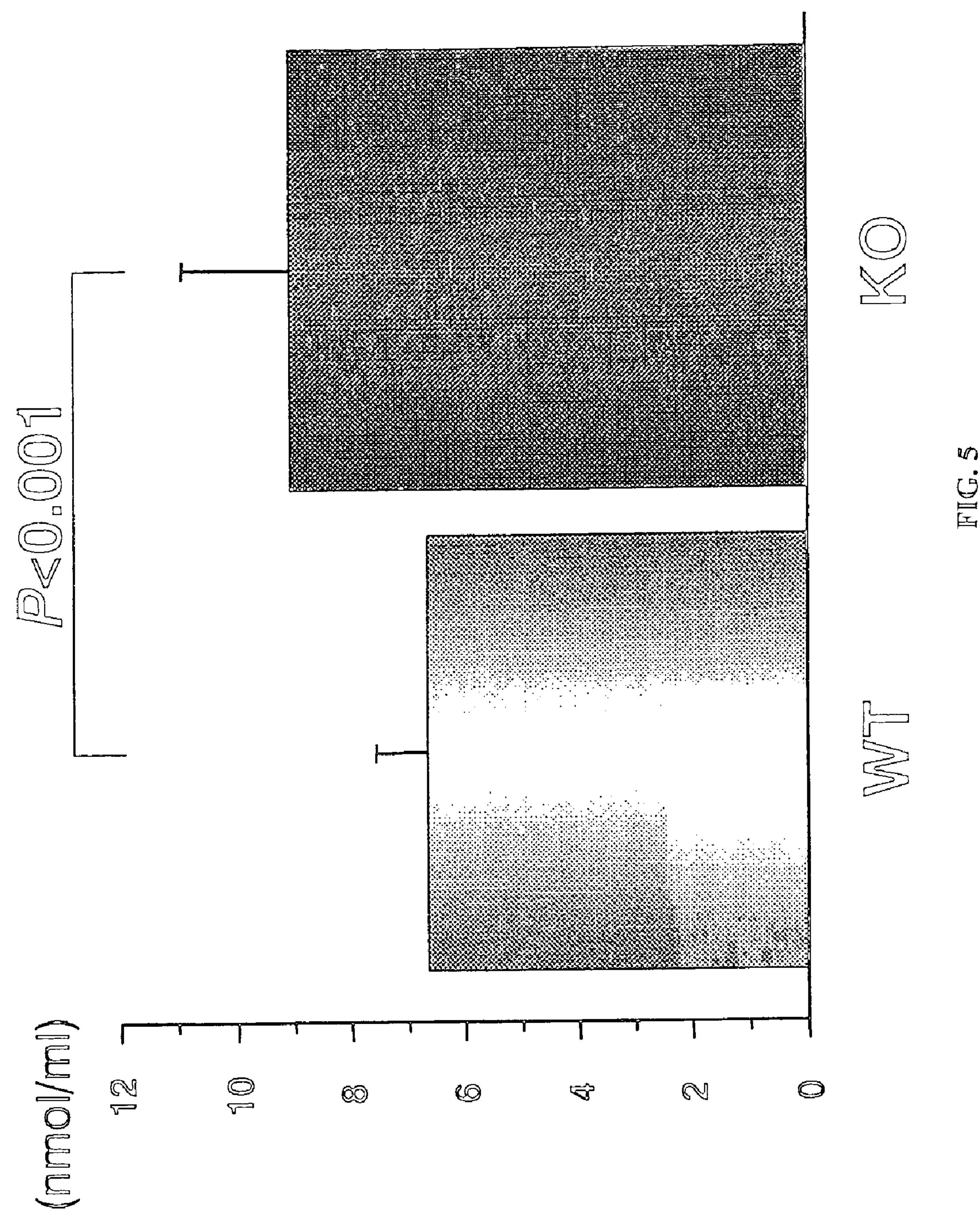
FIG. 5 is a graph showing blood lipid peroxide concentrations after 6 months of administration of the CDAA diet. The blood lipid peroxide concentration was noted to be significantly elevated in KO mice compared to that in WT mice (control mice)
Figure 6:
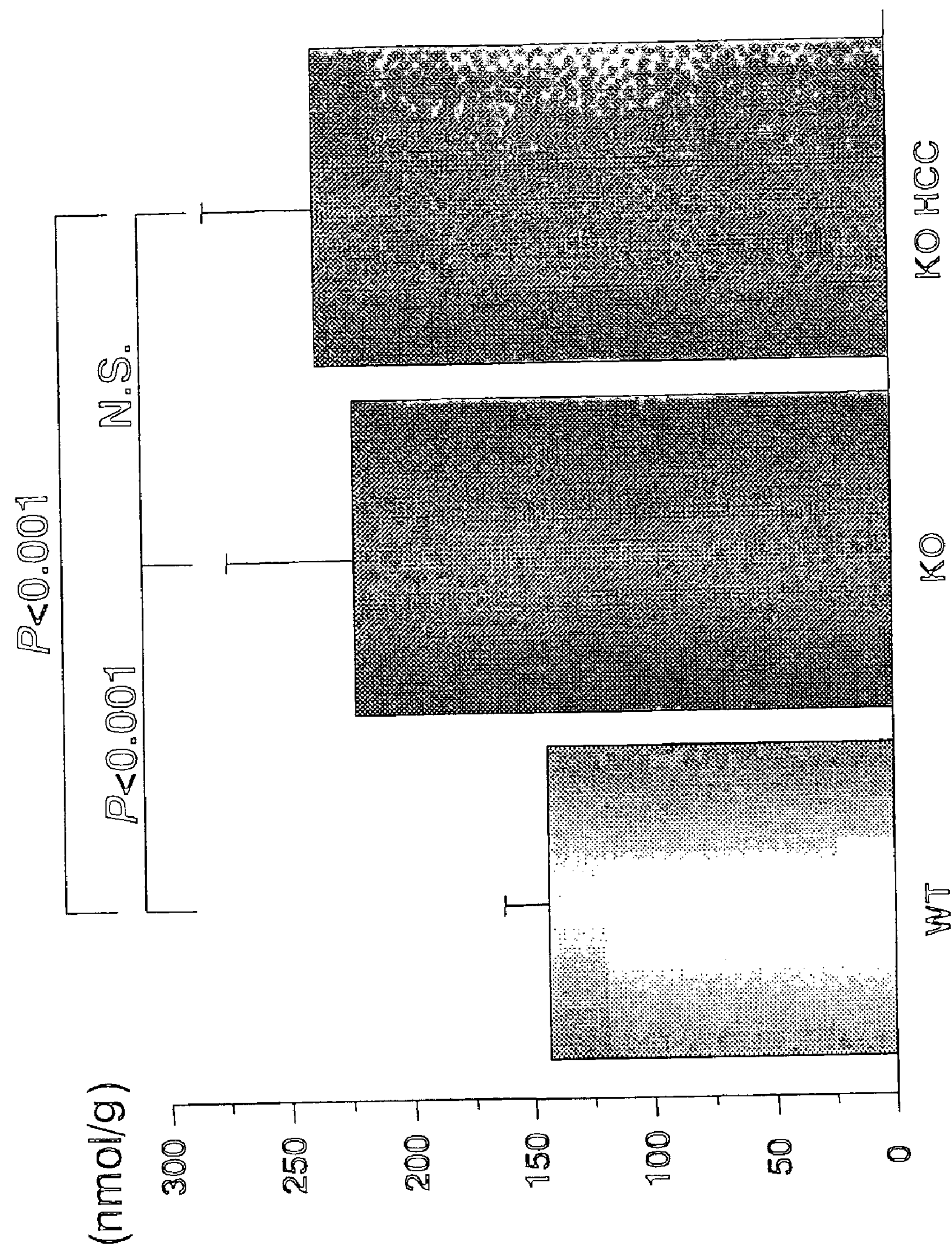
FIG. 6 is a graph showing liver lipid peroxide concentrations after 6 months of administration of the CDAA diet. The liver lipid peroxide concentration was noted to be significantly elevated in KO mice compared to that in WT mice (control mice), but no difference was observed between the tumorized liver and normal liver of KO mice.

Adiponectin is a protein which is produced in the adipose tissue of animals including humans and is present in abundance in blood. Highly purified human adiponectin has been obtained from cDNA encoding this protein by a recombinant method (Arita et al., supra). The nucleotide sequence of cDNA for human adiponectin has been registered in GenBank under the Accession Number D45371. Adiponectin is composed of a collagen-like fibrous domain and a Clq-like globular domain (Waki, H. et al., J. Biol. Chem., 2003, 278, 40352-40363). For example, adiponectin is present in a unique multimer form, which has been shown to be more active than low molecular weight forms (Pajvani, U. B. et al., J. Biol. Chem., 2003, 278, 9073-85; Matsuzawa, Y., Atherosclerosis Supplements, 6, 2005, 7-14).

Also, a substance called ACRP30, cloned from mouse 3T3-F442A cells (Scherer. P E, et al. J. Biol. Chem. 270:26746-26749 (1995)), is thought to be the same entity as adiponectin. This substance has been also obtained with high purity by a technique using the recombinant gene thereof and can be used in the same way as the former. Eight mutations of the adiponectin gene have been reported, some of which are significantly related to diabetes and hyperlipidemia (Matsuzawa, Y., Atherosclerosis Supplements, 6, 2005, 7-14). Proteins comprising an amino acid sequence having a deletion, substitution, or addition of one or several amino acids and having anti-tumor activity also fall within adiponectin of the invention.

As used herein, "anti-tumor activity" refers to an activity to inhibit cancer proliferation, an activity to reduce cancer, and/or an activity to prevent cancer development. In this respect, cancer and tumor are interchangeably used herein. In cultured hepatic stellate cells, adiponectin suppressed platelet-derived growth factor-induced proliferation and migration and attenuated the effect of transforming growth factor-β1 on the gene expression of transforming growth factor-β1 and connective tissue growth factor and on nuclear translocation of Smad2 (Kamada, Y. et al., Gastroenterology, vol. 125, 2003, pages 1796-1807).

The subject to which the anti-tumor agent according to the invention is to be administered is not restricted, but in particular, a patient at high risk of developing a tumor such as an obese patient is suitable. Administration to a patient who has already developed a tumor is also useful, as this may suppress the progression of the tumor. Tumors targeted for the administration may be benign or malignant, and include, various organ tumors (organ cancers), for example, liver cancer (liver tumor), lung cancer (lung tumor), colon cancer, stomach cancer, breast cancer, pancreas cancer, uterine cancer, and the like; however, among these, a liver tumor or liver cancer is particularly responsive.

An anti-tumor agent according to the invention may be administered systemically or locally. Systemic administration includes parenteral treatments such as intravenous, subcutaneous, and intramuscular injections, oral administration, and the like, and can also employ the method of substantially producing adiponectin in the body, e.g., through so-called gene therapy.

Pharmaceutical formulations according to the invention include solutions such as injections, solid preparations such as powders, granules, tablets, capsules, and suppositories, and the like.

Compositions prepared for parenteral administration to humans include injections, suppositories, and the like. When prepared in the form of an injection, the composition may use, for example, solvents (distilled water for injection, etc.), stabilizing agents (sodium edetate, etc.), tonicity agents (sodium chloride, glycerin, mannitol, etc.), pH adjustors (hydrochloric acid, citric acid, sodium hydroxide, etc.), and suspending agents (methylcellulose, sodium carboxymethylcellulose, etc.), and, when prepared in the form of suppositories, may selectively use, for example, suppository bases (cacao butter, macrogol, etc.) and the like appropriately.

Compositions administered orally to humans include, for example, powders, granules, tablets, capsules, syrups, solutions, and the like. When manufactured, e.g., in the form of a powder, granule, or tablet, the composition may use any pharmaceutical carrier suitable for manufacturing solid compositions, for example, an excipient (starch, corn starch, glucose, fructose, saccharose, etc.), lubricant (magnesium stearate, etc.), disintegrator (starch, crystalline cellulose, etc.), binder (starch, gum arabic, etc.) or the like, and can be coated with appropriate coating agents (gelatin, saccharose, gum arabic, carnauba wax, etc.), enteric coating agents (e.g. cellulose acetate phthalate, methacrylate copolymer, hydroxypropylcellulose phthalate, carboxymethylethylcellulose, etc.), or the like. As coating agents for sustained release preparations (DDS preparations), hydroxypropyl methylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit® (methacrylate-acrylate copolymer from Rohm Co., Ltd., Germany), and the like may be used. When made into capsules, such a composition is packed after uniformly mixing with appropriate excipients, for example, magnesium stearate, calcium stearate, talc, light anhydrous silicic acid, or the like for enhancing fluidity and lubricity, crystalline cellulose, lactose, or the like for fluidity under pressure, and, if needed, the above-described disintegrators, or after making the mixture into a granular form, or after applying coating on the granules using an appropriate coating agent, or also after subjecting the mixture or granules to encapsulation molding with an appropriate capsule base (gelatin, etc.) to which glycerin, sorbitol, or the like has been added to increase plasticity. To these capsules may be optionally added a colorant, a preservative (sulfur dioxide, parabens (methyl, ethyl or propyl parahydroxybenzoate, etc.)), and the like. In addition to a common capsule, the capsule may be capsule having an enteric coating, a gastric-resistant capsule, or a controlled-release capsule. When made into enteric coating capsules, liposomes coated with an enteric coating agent may be packed in a common capsule, or a capsule itself may be coated with the enteric coating agent or molded using an enteric polymer as its base. In addition, when the composition is prepared in the form of a syrup or solution, for example, stabilizers (edetate sodium, etc.), suspending agents (gum arabic, carmellose, etc.), flavoring agents (simple syrup, glucose, etc.), aromatics, and the like may be selectively used appropriately.

The dosage varies depending on the type of disease, the sex and age of a patient, the severity of the disease, the administration form, the route of administration, and the like, but, in the case of intravenous injection for inhibiting liver carcinogenesis, it is 1 to 100 mg/kg/day, preferably 3 to 20 mg/kg/day per adult patient. The administration is preferably carried out by adjusting the dosage according to the blood concentration of adiponectin in a subject, and can be performed once daily, or twice to thrice daily in divided doses.

EXAMPLE 1

The present invention is concretely described below, based on a Test Example and Formulation Examples.

Test Example

1. Materials and Methods

A test was carried out using 8-week old adiponectin knockout mice (hereinafter referred to as "KO mice") as test animals, and 8-week old normal mice as control animals. KO mice were prepared according to the method of Maeda et al. (Maeda N, et al. Nat. Med. 8:731-732, 2002).

The test was conducted as described below. The KO mice and the normal mice were fed with a choline-deficient, amino acid-defined diet (CDAA diet: Nakae D, et al. Cancer Res. 52:5042-5045, 1992) in place of a general diet from the time of 8 weeks in age, and killed 1, 3, or 6 months later to observe the presence of the development of liver cell tumors. The mice to which the CDAA diet was administered for 6 months were also determined for the content of lipid (total cholesterol, triglyceride, and free fatty acid) and the amount of lipid peroxide in the liver (the number of individuals: n=14). In this respect, the lipid in the liver was extracted with chloroform/methanol, followed by determination using the Model 7170 automated analyzer from Hitachi Ltd., and the lipid peroxide was determined using a lipid peroxide measuring kit (from Waco).

2. Test Results

The incidence rate of liver cell tumors in each group of mice is shown in Table 1, and the content of lipid in the liver of each group of mice in Table 2.

TABLE 1

Incidence of liver cancer due to a CDAA diet

| | 1 month | 3 months | 6 months |
|---|---|---|---|
| control mice, male | 0/6 | 0/6 | 0/14 |
| control mice, female | 0/5 | 0/5 | 0/14 |
| KO mice, male | 0/6 | 0/6 | 6/14 |
| KO mice, female | 0/6 | 0/6 | 2/14 |

The value within each cell shows the number of tumor-bearing mice/the number of mice tested.

TABLE 2

| Lipid content in the liver after CDAA diet administration | | | |
|---|---|---|---|
| | total cholesterol (mg/g (wet weight)) | triglyceride (mg/g (wet weight)) | free fatty acid (μEq/g (wet weight)) |
| control mice | 2.1 ± 0.436 | 112.825 ± 44.4 | 5.133 ± 1.258 |
| KO mice | 2.367 ± 0.115 | 131.900 ± 115.918 | 4.025 ± 1.053 |
| Significant difference (5%) | N.S. | N.S. | N.S. |

The value within each column shows mean±SD.

It is known that the CDAA diet disturbs the production of VLDL from lecithin in the liver, causing marked fatty liver due to the accumulation of triglyceride in liver cells, and resulting in the appearance of a liver tumor about one year later. Then, female mice have been also shown to have a lower cancer incidence rate than male mice. However, in the group of KO mice given the CDAA diet, even after a period of administration of only 6 months, the development of a liver tumor (liver cell cancer) was observed in 6 of 14 males and in 2 of 14 females. Thus, it has been demonstrated that a deficiency of adiponectin in blood shortens the period prior to the appearance of a tumor and promotes carcinogenesis in the liver. From this fact, it may be deduced that administration of adiponectin inhibits carcinogenesis, particularly in the liver.

Formulation Example 1

Injection

| | |
|---|---|
| adiponectin | 2 mg |
| phosphate buffer | appropriate amount (pH 7.0) |
| | total: 1 ml |

This is placed in a 2-ml glass ampoule, sealed and sterilized.

Formulation Example 2

Tablet (Enteric Coated Tablet)

| | |
|---|---|
| adiponectin | 0.8 g |
| corn starch | 12 g |
| lactose | 27.2 g |
| magnesium stearate | 0.4 g |

Adiponectin, lactose, and corn starch are thoroughly admixed to give granules for tableting according to a wet tablet preparation method. Magnesium stearate is added and the mixture is tableted to give 400 tablets. The tablets are coated with an enteric coating agent (methacrylic acid copolymer).

The above non-limiting examples are shown in order that the present invention may be more readily understood. From the above description, one can ascertain the essential characteristics of the present invention and, without departing from the spirit and scope thereof, can make various changes and modifications of the invention to adapt it to various uses and conditions.

The invention claimed is:

1. A method for treating a liver cancer by administering to a patient in need thereof an effective amount of adiponectin, wherein the dosage of said adiponectin is 1 to 100 mg/kg/day per adult patient.

2. The method according to claim 1, wherein adiponectin is administered in the form of an injection.

* * * * *